United States Patent [19]

Rodriguez Otero et al.

[11] Patent Number: 6,100,052
[45] Date of Patent: *Aug. 8, 2000

[54] PROCESS FOR THE PRODUCTION OF CLAVULANIC ACID AND/OR SALTS THEREOF BY FERMENTATION CONTROLLING SOLUBLE PHOSPHATE CONCENTRATION

[75] Inventors: Carmelita Rodriguez Otero; Miguel Angel Moreno Valle; Manuel Jesus Lopez Nieto; Alfonso Juan Collados De La Vieja; Alejandro Vitaller Alba, all of Leon, Spain

[73] Assignee: Antibioticos, S.A., Madrid, Spain

[*] Notice: This patent issued on a continued prosecution application filed under 37 CFR 1.53(d), and is subject to the twenty year patent term provisions of 35 U.S.C. 154(a)(2).

[21] Appl. No.: 08/875,189
[22] PCT Filed: Nov. 15, 1996
[86] PCT No.: PCT/ES96/00215
  § 371 Date: Sep. 15, 1997
  § 102(e) Date: Sep. 15, 1997
[87] PCT Pub. No.: WO97/19187
  PCT Pub. Date: May 29, 1997

[30] Foreign Application Priority Data

Nov. 23, 1995 [ES] Spain ................................ P9502300

[51] Int. Cl.⁷ ..................................................... C12P 37/00
[52] U.S. Cl. ............................ 435/43; 435/118; 435/119; 435/120; 435/886

[58] Field of Search ............................... 435/43, 119, 118, 435/120, 886

[56] References Cited

U.S. PATENT DOCUMENTS 4,110,165  8/1978  Cole ........................................ 435/119

FOREIGN PATENT DOCUMENTS 0182522  5/1986  European Pat. Off. .
1508977  4/1978  United Kingdom .

OTHER PUBLICATIONS

Fang et al., J. Ind. Microbiol., vo. 15 (5), p. 407–410, 1995.
Romero, J. Et al. "Dissociation of cephamycin and clavulanic acid biosynthesis in Streptomyces Clavuligerus." Applied Microbiology and Biotechnology, vol. 20 (1984), pp. 318–325.
Lebrihi, A. Et al. "Phosphate repression of cephamycin and clavulanic acid production by Streptomyces clavuligerus." Applied Microbiology and Biotechnology, vol. 26, (1987), pp. 130–135. AT 400846 B (Fermic S.A.) Feb. 15, 1996.

*Primary Examiner*—Irene Marx
*Attorney, Agent, or Firm*—Ladas & Parry

[57] ABSTRACT

A batch fermentation is carried out continuously or semi-continuously using strain of *Streptomyces clavuligerus* for the production of clavulanic acid. The fermentation process is carried out with strict control of the soluble phosphate in the medium both at the beginning and throughout the process.

19 Claims, No Drawings

PROCESS FOR THE PRODUCTION OF CLAVULANIC ACID AND/OR SALTS THEREOF BY FERMENTATION CONTROLLING SOLUBLE PHOSPHATE CONCENTRATION

This application was filed under 35 USC 371 as the national phase of PCT/ES96/00215 filed Nov. 15, 1996.

A process is described for the production of clavulanic acid and/or its salts by means of a fermentation with selected strains of Streptomyces clavuligerus with a strict control of the concentration of soluble phosphate present during the fermentation and with the optional use of carbon sources such as lipids, preferably triglycerides.

PRIOR ART

Clavulanic acid is a molecule of formula

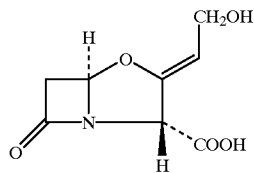

whose usefulness is based on its capacity to inhibit the enzymes called beta-lactamases, which are possessed by some Gram-positive and Gram-negative pathogenic microbes such as Escherichia coli, Klebsiella aerogenes, and the like, and which, due to their action, endows them with resistance to some beta-lactam antibiotics. As a result, clavulanic acid mixed with the said antibiotics increases their antibacterial spectrum.

It is known that the production of clavulanic acid is performed by several strains belonging to the genus Streptomyces, such as, for example, Streptomyces clavuligerus ATCC 27064, Streptomyces jumonjinensis NRRL 5741, and the like.

As has already been disclosed in earlier patents (European Patent 0,182,522 B1), the production of clavulanic acid may be increased in batch fermentation when an assimilable carbon source such as, for example, glycerol or maltose is added during the fermentation also instead of only being added initially. However, this increase in production obtained in this way is fairly low. Accordingly, an objective of the present invention is to procure a process for obtaining clavulanic acid and/or its salts with a production which is plainly greater than that obtained by the processes known in the prior art.

Many authors have demonstrated the inhibitory effect of phosphate on the production of antibiotics (Martín, J. F., 1977, Adv. Biochem. Eng. 6:105–127). Specifically, an inhibition of phosphate on the synthesis of cephalosporins by Streptomyces clavuligerus has been found (Lübbe, C. et al. 1985, Arch. Microbiol. 140:317–320 and Lübbe, C. et al. 1984, FEMS Microbiol. Lett. 25:75–79; Aharonowithz, Y. et al. 1977, Arch. Microbiol. 115:169–173; Jhang, J. et al. 1989, FEMS, 57:145–150), and also an inhibitory effect of phosphate on the synthesis of clavulanic acid by the said microorganism (Lebrihi, A. et al. 1987, Appl. Microbiol. Biotechnol. 26:130–135; Romero, J. et al. 1984, Appl. Microbiol. Biotechnol. 20:318–325). However, contrary to the findings reported in the above papers, we have found, surprisingly, instead of a negative effect of phosphate on the production of clavulanic acid, a substantial increase in the production of clavulanic acid and/or its salts when the soluble phosphate level in the culture medium reaches an optimal range and is maintained in the said range. What is more, we have found that a strict control of the concentration of soluble phosphate in the culture medium has a greater influence on the increase in production of the system than the actual addition of nutrients. A batch or semi-continuous (fed-batch) culture of Streptomyces clavuligerus was used for the production of clavulanic acid, as well as other antibiotics or molecules typical of secondary metabolism. For the purposes of this specification, the term batch culture indicates a fermentation in which the nutrients are introduced into the culture medium only initially and the broth is extracted from the fermentation tank only at the end of the process. The term semi-continuous (fed-batch) culture implies a fermentation in which the nutrients are introduced into the culture medium not only initially, but also throughout the fermentation, and the broth is extracted from the fermentation tank only at the end of the process. The process of batch or fed-batch production of clavulanic acid displays some special features of fermentation, so that a significant increase in viscosity is initially produced, with the resulting difficulty of maintaining an acceptable level of dissolved oxygen for prolonging the production phase for longer periods of time. Consequently, a fragmentation of the mycelium, a decrease in viscosity and a reduction in production occur, ending of the process being unavoidable.

Continuous culture is preferentially applied for obtaining biomass, amino acids and other primary metabolites (Hospodka, J. 1966, Theoretical and Methodological Basis of Continuous Culture of Microorganisms, pp 493–645; Malek, J and Fencl, Z. eds. Academic Press New York). However, the use of a continuous culture for obtaining secondary metabolites (antibiotics) has not really been described, or has been carried out with limited efficacy (Vu-Trong, K. and Grey, 1982 Biotechnol. Bioengineering 24: 1093–1103; Trangott C. S. et al. 1993 Apol. Microbiol. Biotechnol. 39:433–437; Noack. D. 1988, J. Bas. Microbiol. 28:101–106). For the purposes of the present specification, the term continuous culture implies a fermentation in which the nutrients are introduced into the culture medium both at the beginning and also throughout fermentation, and some portions of broth are extracted from the fermentation tank throughout the fermentation and not only at the end of the latter. We have now found that, by adding soluble phosphate to the culture medium and/or controlling and fixing its concentration throughout the fermentation, it is possible and advantageous to obtain clavulanic acid and/or its salts in continuous culture with a high production. In the continuous process, by means of suitable dilution of the culture, the viscosity reduces progressively throughout the process, enabling the concentration of dissolved oxygen to be maintained (>40%) for longer periods of time without an increase in agitation, avoiding fragmentation of the mycelium and prolonging the period of production of clavulanic acid. As a consequence of the addition of nutrients and water, complete filling of the installed capacity is achieved, which requires continuous extraction of the broth throughout the fermentation process, either intermittently or continuously, in order to maintain the appropriate working volume. In this way, and by controlling the process by adding soluble phosphate to the culture medium throughout the process, a lengthening of the fermentation cycle and an increase in total production achieved are obtained, increasing in turn the production yield per geometrical installed capacity.

DESCRIPTION OF THE INVENTION

Accordingly, the present invention provides a process for producing clavulanic acid and/or its salts, by culturing selected strains of *Streptomyces clavuligerus* ATCC 27064 and/or mutants thereof, in submerged fermentation with aeration and agitation, in batch, semi-continuous or continuous culture, in which the concentration of soluble phosphate present in the culture medium initially and throughout fermentation is fixed and/or maintained within set ranges, depending on each type of culture employed, 500 to 4000 mg/l at the beginning of the fermentation in batch culture or, in the case of semi-continuous (fed-batch) or continuous culture, between 150 and 600 mg/l at the beginning of the fermentation and between 20 and 150 mg/l throughout the latter.

The process for the production of clavulanic acid and/or its salts according to the present invention is carried out in the presence of assimilable C and N sources and, optionally, of inorganic salts. The fermentation is carried out under aerobic conditions and in submerged culture.

The optimal fermentation temperature preferentially lies between 20° C. and 40° C., especially between 22° C. and 30° C.

The C sources may be added as simple or complex nutrients, only initially (in the case of a batch culture) or throughout the fermentation by means of intermittent or continuous additions, in the case of semicontinuous (fed-batch) or continuous culture, respectively. Depending on the strain used, these C sources include carbohydrates (dextrins, starches, maltose, and the like), polyols such as glycerol, for example, lipids (chiefly triglycerides, either natural or synthetic) and, in general, any other C source which permits the growth of microorganisms. We have found specifically that lipids, and more especially natural or synthetic triglycerides, can be regarded as one of the preferred sources for carrying out the process of the invention, while there are no references to this effect in the prior art. In fact, we have found that, using such carbon sources, even only by means of a single initial addition to the culture medium (batch culture), the production of clavulanic acid and/or its salts can be manifestly increased simply by taking care that the concentration of soluble phosphate remains within the limits defined in the present invention.

The culture medium should also carry an assimilable source of organic or inorganic N, such as, for example, soya-bean meal, corn-steep liquor, soluble distillates, yeast extracts, cotton-seed flour, peptone, casein or ammonium sulphate.

Various inorganic salts, such as sodium, potassium, ammonium, iron, calcium and magnesium, chlorides, sulphates and phosphates, may also be incorporated in the culture medium.

The clavulanic acid concentration may be determined microbiologically by employing a microbe producing beta-lactamase, such as, for example, *Klebsiella aerogenes*, although it is preferable to carry out the determination using high performance liquid chromatography.

The extraction of clavulanic acid or its salts from the broth may be performed in the manner in which other antibiotics, specifically other beta-lactams, are extracted, employing ion exchange resins or solvents or any other of the known conventional methods.

The soluble phosphate in the initial medium may be determined by a simple and rapid procedure, for example by means of a commercial kit (Boehringer Mannheim Automated Analysis for BM/Hitachi System 704). The principle of the method is the reaction of inorganic phosphorus with ammonium molybdate. This inorganic phosphorus is then expressed as phosphate. To analyse the soluble phosphate, the sample (taken homogeneously from the culture broth) should be filtered beforehand through a Millipore filter of pore size 0.45 μm or similar, in order to remove solids. This sample should be taken after the sterilization of the culture medium, since the concentration of soluble phosphate may fluctuate in accordance with the sterilization process. Samples may also be taken throughout the fermentation process.

The assay of total phosphate is carried out by taking 1 ml of total broth and adding 1 ml of sulphuric acid and 5 ml of nitric acid. This solution is evaporated by heating until it has a final volume of 1 ml of a transparent solution. This final volume is brought to 25 ml with distilled water and assayed by the above-mentioned method for soluble phosphate.

When the fermentation is carried out batchwise, it has been found that the optimal level of soluble phosphate at the beginning of the fermentation shall be between 500 and 4000 mg/l, and preferably between 800 and 1600 mg/l.

If, owing to the nature of the starting materials used and to their concentration, the level of soluble phosphate is well above or below these limits, it should be corrected. To this end, when the level is below the lower limit, more inorganic phosphate may be added before or after the sterilization, for example in the form of potassium or sodium salt, until the desired level is reached. Alternatively, part of the soluble phosphate may be precipitated if its level is very high by adding any precipitant, for example by means of a calcium compound such as a calcium hydroxide or acetate, or by any other system which ensures that this objective is attained.

According to the present invention, an up to 5-fold increase in production has been observed compared with a fermentation system without control of the initial soluble phosphate in the medium in batch culture. Table I shows the results of several fermentations carried out with the optimal level of soluble phosphate, and outside this level.

TABLE I

| Fermentation No. | Soluble phosphate mg/l | Clavulanic acid | | | |
|---|---|---|---|---|---|
| | | 72 h μg/ml | % | 96 h μg/ml | % |
| 1 (comparative) | 18 | 311 | 100 | 420 | 100 |
| 2 (comparative) | 100 | 560 | 180 | 790 | 188 |
| 3 | 900 | 1410 | 453 | 2210 | 526 |
| 4 | 1580 | 1550 | 495 | 2240 | 533 |
| 5 | 3000 | 1410 | 453 | 1750 | 416 |
| 6 (comparative) | 7000 | 410 | 131 | 780 | 186 |

Percentage increase (%) is understood to mean the production of clavulanic acid and/or its salts, expressed as the result of multiplying the final value in μg/ml by 100 and dividing this figure by 311 (in the case of a 72 h incubation) or by 420 (at 96 h), which represent the results of the fermentation in which the soluble phosphate levels lie outside the optimal range.

This phosphate should be soluble in the fermentation broth, as is reflected in the following results in Table II, in which similar levels of total phosphate lead to fermentations with very disparate results depending on whether the soluble phosphate is or is not within the optimal limits.

TABLE II

| Fermentation No. | Soluble phosphate mg/l | Total phosphate mg/l | Clavulanic acid μg/ml (96 h) |
|---|---|---|---|
| 4 | 1580 | 2380 | 2240 |
| 7 (comparative) | 230 | 2265 | 920 |

The difference in growth of the microorganism for different phosphate levels does not appear to be responsible for the difference in production, at least as a main factor. In Table III, it may be observed that there are different levels of production for similar growths, so that the phosphate level appears once again to be the cause of the increase in production. The mycelial volume has been determined in a centrifuge at 2500 g for 10 minutes. (g denotes force of gravity.)

TABLE III

| Fermentation No. | Soluble phosphate mg/l | % Mycelial vol. 72 h | % Mycelial vol. 96 h | Clavulanic acid 72 h | 96 h μg/ml |
|---|---|---|---|---|---|
| 1 (comparative) | 18 | 23 | 22 | 311 | 420 |
| 2 (comparative) | 100 | 22 | 22 | 560 | 790 |
| 3 | 900 | 30 | 30 | 1410 | 2210 |
| 4 | 1580 | 30 | 30 | 1550 | 2240 |
| 5 | 3000 | 30 | 30 | 1410 | 1750 |
| 6 (comparative) | 7000 | 27 | 28 | 410 | 780 |

During the period of fermentation, it is possible to carry out a process of fed-batch addition of phosphate, and also of the remainder of the nutrients, distributed throughout the whole fermentation. It has been found that the optimal level of total soluble phosphate (initial and added) is slightly less than the level in the batch mode, lying between 400 and 2000 mg/l.

This input should be effected in such a way that the initial level is between 150 and 600 mg/l, and that the level of soluble phosphate throughout the fermentaiton is between 20 and 150 mg/l. To this end, it is appropriate to effect an input of soluble phosphate ion or any precipitant calcium compound, as in the case of batch fermentation, depending on whether it is required to raise or lower the phosphate level, respectively, in order to maintain it within the indicated limits. Table IV shows the results of several semi-continuous fermentations carried out with different concentrations of soluble phosphate, present initially and added.

It may be observed that the total amount of added phosphate is considerably higher, without impairing production, when the said addition is carried out throughout the fermentation instead of initially. All the tests carried out maintained the concentration of soluble phosphate throughout the fermentation at the indicated level, except for fermentations Nos 8, 9 and 10, in which the level was lower than that required, and No. 16 in which the level was higher.

TABLE IV

| Fermentation No. | SOLUBLE PHOSPATE (mg/l) Initial concentration | SOLUBLE PHOSPATE (mg/l) Total added | CLAVULANIC ACID μg/ml | CLAVULANIC ACID % |
|---|---|---|---|---|
| 8 | 80 | 0 | 990 | 33 |
| 9 | 265 | 0 | 1230 | 41 |
| 10 | 520 | 0 | 2400 | 80 |
| 11 | 990 | 0 | 2080 | 69 |
| 12 | 1530 | 0 | 1920 | 64 |
| 13 | 228 | 618 | 3000 | 100 |
| 14 | 510 | 570 | 4020 | 134 |
| 15 | 722 | 594 | 3270 | 109 |
| 16 | 950 | 603 | 2730 | 91 |
| 17 | 278 | 1710 | 3600 | 120 |
| 18 | 230 | 2280 | 3360 | 112 |

In continuous culture, by means of suitable dilution of the culture, the viscosity reduces progressively throughout the process, enabling the concentration of dissolved oxygen to be maintained (>40%) for longer periods of time without an increase in agitation, avoiding fragmentation of the mycelium and prolonging the period of production of clavulanic acid. As a consequence of the addition of nutrients and water, complete filling of the installed capacity is achieved, which requires continuous extraction of the broth in order to maintain the appropriate working volume. In this way, and by controlling the process by adding soluble phosphate to the culture medium throughout the process, a lengthening of the fermentation cycle and an increase in total production achieved are obtained, increasing in turn the production yield per geometrical installed capacity.

In continuous culture, as in the previous cases, in batch and semi-continuous modes, an initial addition of soluble phosphate is carried out. This addition is generally less than that for the batch and semi-continuous cultures, and is of the order of 150 to 600 mg/l, preferably an initial 200 to 400 mg/l, a subsequent level in the broth of the same order, 20–150 mg/l, being maintained for a longer time (50–100 hours).

In continuous cultures, as in the batch or semi-continuous fermentation, inputs of soluble phosphate salts or calcium compounds or other efficient sequestering agents are effected in order to establish the requisite initial concentrations in each case and to maintain the desired concentration during the fermentation. The addition of total soluble phosphate salts is similar or slightly greater than that used in semi-continuous fermentation.

Water is, moreover, added to the culture medium from 32 hours onwards, with the object of maintaining the viscosity of the broth at values below 700 cP, which permits an increase in the amount of nutrients added in the traditional systems, maintaining the level of dissolved oxygen above 40%, and of prolonging the production of clavulanic acid up to 150–170 hours.

During the complete process, a total dilution of 1.5 to 1.6 is generally achieved, against 0.9 to 1.1 for the traditional cultures, making the installed geometric capacity economically viable. The process is carried out by adding nutrients to the initial medium continuously throughout the fermentation. These nutrients are chiefly the carbon source. From 100 hours onwards, continuous or intermittent extraction of the broth is carried out in a proportion of 2.5 to 14% of the volume of the fermenter per day, with the object of keeping the volume constant and the viscosity of the medium to below 700 cP. The process may be prolonged up to 160–170 hours.

Examples 19–25 are reproduced in Table V, with fed-batch and continuous cultures, with different nutrients and different levels or inputs of soluble phosphate.

TABLE V

| No. | FERMENTATION | AGE (h) | SOLUBLE PHOSPHATE mg/l | | ADDITION NUTRIENTS | DILUTION | EXTRACTION 100 h. % DAY (V.A.S) | CLAVULANIC µg/ml | ACTIVITY K/m³g |
|---|---|---|---|---|---|---|---|---|---|
| | | | INITIAL | ADDITION | | | | | |
| 19 | Semi-continuous | 132 | 150 | 720 | Weichol-92 | 0.96 | — | 3150 | 1.63 |
| 20 | " | 135 | 241 | 550 | Soya-bean oil | 1.10 | — | 3710 | 2.20 |
| 21 | Continuous | 172 | 495 | 625 | Priol. + glycerol | 1.32 | 2.5% | 3890 | 2.77 |
| 22 | " | 150 | 475 | 1080 | " | 1.40 | 9% | 2445 | 1.85 |
| 23 | " | 172 | 500 | 1120 | " | 1.61 | 14% | 2870 | 2.49 |
| 24 | " | 155 | 445 | 1145 | " | 1.57 | 14% | 2680 | 2.27 |
| 25 | " | 150 | 260 | 1560 | Priolube | 1.42 | 9% | 2660 | 2.06 |

WEICHOL-92 ®, Synthetic Triglyceride INDUSTRIA QUIMICA LASSEM
PRIOLUBE ®, Glyceryl trioleate UNICHENTA (HOLLAND)
V.A.S. Volume After Sterilization By way of illustration, the following examples are described:

EXAMPLE 1 (Comparative)

An inoculation medium with the following composition is prepared:

| | |
|---|---|
| Fish meal | 2 g |
| Glycerol | 1.5 g |
| Soluble starch | 1.5 g |
| Calcium carbonate | 0.2 g |
| Distilled water | q.s. 100 ml |

The pH is adjusted to 6.7 and the medium is distributed in 250-ml Erlenmeyer flasks in the proportion of 40 ml per flask. The flasks are stoppered and sterilized at 121° C. for 20 minutes.

The medium thus prepared is inoculated with a suspension of spores of a mutant strain that overproduces clavulanic acid, obtained by means of a step of mutation of Streptomyces clavuligerus ATCC 27064 with N-methyl-N'-nitro-N-nitrosoguanidine and several steps of mutation with ultraviolet light. This suspension is prepared from a slant or plate, with a nutrient medium capable of permitting growth and sporulation.

After inoculation, the medium is incubated for 2 days at 25° C. on a rotary agitator with an eccentricity of 5 cm at 250 rpm.

This culture thus prepared is employed to inoculate in the proportion of 5% a fermentation medium with the following composition:

| | |
|---|---|
| Soya-bean meal | 4 g |
| Maize dextrin | 1 g |
| MOPS buffer (3-[N-morpholino] propanesulphonic acid) | 1 g |
| Calcium chloride | 10 mg |
| Sodium chloride | 10 mg |
| Magnesium chloride | 10 mg |
| Sodium acetate | 0.1 g |
| Soya-bean oil | 2 g |
| Distilled water | q.s. 100 ml |

The pH of the medium is adjusted to 7.0 and the medium is distributed in 250-ml flasks in the proportion of 30 ml per flask. The flasks are stoppered and sterilized for 20 minutes at 121° C. After sterilization, the soluble phosphate is measured in one of the flasks, a value of 100 mg/l being obtained.

By way of example and in order to illustrate the results of fermentation No. 1 shown in Table I, 0.5 ml of 0.5% calcium hydroxide solution was added to each flask. After the addition, the level of soluble phosphate was assayed again in one of the flasks, a value of 18 mg/l now being obtained, at which level the said fermentation No. 1 was carried out.

The fermentation medium thus prepared and inoculated is incubated at 25° C. in a rotary agitator with an eccentricity of 5 cm at 250 rpm. At 96 hours of incubation, the production of clavulanic acid obtained was 420 µg/ml HPLC.

EXAMPLE 2 (Comparative)

The procedure is the same as in the case of Example 1, but addition of calcium hydroxide is not performed. As a result, the fermentation is carried out in a medium with 100 mg/l of soluble phosphate. At 96 hours of incubation, the production of clavulanic acid was 790 µg/ml HPLC (see fermentation No. 2 of Table I).

EXAMPLE 3

The procedure is the same as in the case of Example 1, but in this case addition of calcium hydroxide is not carried out, and 0.12% of monopotassium phosphate, added before adjusting the pH, is included in the formula of the fermentation medium. The soluble phosphate is assayed from one flask after sterilization, and it is established that the fermentation is carried out in a medium with 900 mg/l of soluble phosphate. At 96 hours of incubation, the production of clavulanic acid was 2210 µg/ml HPLC (see fermentation No. 3 of Table I).

EXAMPLE 4

The procedure is the same as in Example 3, but in this case 0.21% of monopotassium phosphate is included in the formula. The soluble phosphate is assayed from one flask after sterilization, and it is established that the fermentation is carried out in a medium with 1580 mg/l of soluble phosphate. In this case the total phosphate was also determined, a value of 2380 mg/l being obtained, as may be seen in Table II. At 96 hours of incubation, the production of clavulanic acid was 2240 μg/ml HPLC (see fermentation No. 4 of Table I).

EXAMPLE 5

The procedure is the same as in Example 3, but in this case 0.4% of monopotassium phosphate is included in the formula. The soluble phosphate is assayed from one flask after sterilization, and it is established that the fermentation is carried out in a medium with 3000 mg/l of soluble phosphate. At 96 hours of incubation, the production of clavulanic acid was 1750 μg/ml HPLC (see fermentation No. 5 of Table I).

EXAMPLE 6 (Comparative)

The procedure is the same as in the case of Example 3, but in this case 0.95% of monopotassium phosphate is included in the formula. The soluble phosphate is assayed from one flask after sterilization, and it is established that the fermentation is carried out in a medium with 7000 mg/l of soluble phosphate. At 96 hours of incubation, the production of clavulanic acid was 780 μg/ml (see fermentation No. 6 of Table I).

EXAMPLE 7 (Comparative)

The process is the same as the one in Example 3, but in this case 0.245% of tribasic calcium phosphate is included in the formula (monopotassium phosphate is not included). The soluble phosphate is assayed from one flask after sterilization, the result of 230 mg/l of soluble phosphate being obtained. In this case the total phosphate was also determined, the result being 2265 mg/l (see fermentation No. 7 of Table II). After 96 hours of incubation, the production of clavulanic acid was 920 μg/ml HPLC.

EXAMPLES 8 to 18 (see Table IV)

An inoculation medium with the same composition as the one described in Example 1 is prepared, and is distributed in 2000-ml Erlenmeyer flasks with 500 ml of medium. The flasks are stoppered and sterilized at 121° C. for 20 minutes.

When inoculation has been performed with a spore suspension similar to the one used in Example 1, the medium is incubated for 2 days at 25° C. on a rotary agitator with an eccentricity of 5 cm at 250 rpm.

400 ml of this culture are taken and used to inoculate a tank with 150 litres of the following medium:

| | |
|---|---|
| Soya-bean meal | 2 g |
| Dextrin | 2 g |
| Monopotassium phosphate | 0.04 g |
| Soya-bean oil | 0.1 g |
| UCON antifoam (Polyalkylene glycol) | 0.1 g |
| Water | q.s. 100 ml |

The pH of the medium is adjusted to 7.3 and the medium is sterilized at 121° C. for 20 minutes. Incubation takes place at 28° C. for about 30 hours, with agitation at 115 rpm, an aeration of 0.5 v/v/min and a dome pressure of 1 kg/cm$^2$.

45 litres of culture incubated under the above conditions are taken and transferred to a tank with 450 litres of the following medium:

| | |
|---|---|
| Soya-bean meal | 4 g |
| Dextrin | 2 g |
| Soya-bean oil | 0.1 g |
| UCON antifoam | 0.1 g |
| Magnesium chloride | 0.02 g |
| Ferric chloride | 0.003 g |
| Calcium chloride | 0.01 g |
| Water | q.s. 100 ml |

The pH of the medium is adjusted to 7.0 and the medium is sterilized at 121° C. for 20 minutes. After sterilization, the soluble phosphate is measured, which in this case gives a result of 200 mg/l to 300 mg/l. If necessary, with the object of obtaining different initial concentrations, this value is adjusted by adding suitable volumes of 1% monopotassium phosphate solution (Examples 10, 11, 12, 14, 15 and 16), or with a calcium compound (Example 8, where the appropriate volume of Ca(OH)$_2$ solution was added). When the soluble phosphate has been adjusted, transfer of the 45 litres of inoculation culture is carried out and fermentation commences. The latter takes place while maintaining a constant temperature of 25° C., 115 rpm, 0.5 v/v/min for the first 24 hours and 1.5 v/v/min from 25 hours up to the end of fermentation, and under a dome pressure of 0.5 kg/cm$^2$.

The different concentrations of soluble phosphate throughout the fermentation were obtained by adding different volumes of sterile 1% monopotassium phosphate solution (Examples 13 to 18).

Automatic control of the pH is performed in order to maintain the latter between 6.8 and 7.2. The following additions are also made:

Soya-bean oil: 100 ml/h from 10 to 120 hours.

33% glycerol: 400 ml/h from 32 to 120 hours.

1% monopotassium phosphate: 400 to 1400 ml/h from 0 to 25 hours and 1500 to 5000 ml/h from 25 to 50 hours.

After 120 h of incubation, the production of clavulanic acid varies between 990 and 4020 μg/ml, in accordance with Table IV.

EXAMPLE 19

The preparation of the media and establishing of the fermentation conditions are carried out as in Examples 8 to 18 (Table IV), but a dextrin concentration of 34 g/l was included in the initial cycle. The addition of glycerol was omitted, and only Weichol-92 (synthetic triglyceride with 60% of oleic acid, manufactured by Industria Química Lassem) and 1% monopotassium phosphate were supplied, with the following programmes of addition:

| | |
|---|---|
| Weichol-92 | 100 ml/h from 10 h to 120 h |
| Monopotassium phosphate (1%) | 400 to 1400 ml/h from 0 to 25 h and 1500 to 5000 ml/h from 25 to 50 h |

EXAMPLE 20

The procedure is the same as in Example 19, but the addition of the synthetic triglyceride Weichol-92 is replaced by that of soya-bean oil.

EXAMPLE 21

The procedure is the same as in Example 19, but the fermentation is extended up to 172 h, the continuous system being established with extractions of total broth from 100 h of fermentation onwards in a proportion of 2.5% of the broth extracted every 24 h relative to the initial volume of the fermenter after sterilization.

Additions of glycerol (33%), Priolube (glyceryl trioleate, manufactured by Unichenta) and monopotassium phosphate (1%) are made according to the programmes:

| | |
|---|---|
| Priolube | 100 ml/h from 10 h to the end |
| Glycerol (33%) | 400 ml/h from 32 h to the end |
| Monopotassium phosphate (1%) | 400 to 1400 ml/h from 0 to 25 h and 1500 to 5000 ml/h from 25 to 50 h |

EXAMPLE 22

The procedure is as in Example 21, but the fermentation is extended only up to 150 h and the extraction of broth is carried out in a proportion of 9% every 24 h. The additions are modified according to the programmes:

| | |
|---|---|
| Priolube | 100 ml/h from 10 h to 100 h |
| | 200 ml/h from 100 h to the end |
| Glycerol (33%) | 420 ml/h from 32 h to 100 h |
| | 780 ml/h from 100 h to the end |
| Monopotassium phosphate (1%) | 400 to 1400 ml/h from 0 to 25 h |
| | 1500 to 5000 ml/h from 25 to 50 h |
| | 300 ml/h from 50 h to the end |
| Sterile water | 312 ml/h from 32 to 100 h |
| | 625 ml/h from 100 h to the end |

EXAMPLE 23

The procedure is as in Example 22. The fermentation is extended to 172 h with an extraction of 14% every 24 h. A programme of addition of sterile water is also included in order to maintain the viscosity level low.

| | |
|---|---|
| Priolube | 130 ml/h from 10 h to 100 h |
| | 240 ml/h from 100 h to the end |
| Glycerol (33%) | 515 ml/h from 32 h to 100 h |
| | 960 ml/h from 100 h to the end |
| Monopotassium phosphate (1%) | 400 to 1400 ml/h from 0 to 25 h |
| | 1500 to 5000 ml/h from 25 to 50 h |
| | 300 ml/h from 50 h to the end |
| Sterile water | 630 ml/h from 32 to 100 h |
| | 1260 ml/h from 100 h to the end |

EXAMPLE 24

The procedure is as in Example 23, but the initial fermentation medium is increased by 30% with respect to all its starting materials. The fermentation reaches 155 h and the extraction carried out is of 14% every 24 h. The programmes of addition used are:

| | |
|---|---|
| Priolube | 130 ml/h from 10 h to 100 h |
| | 240 ml/h from 100 h to the end |
| Glycerol (33%) | 515 ml/h from 32 h to 100 h |
| | 960 ml/h from 100 h to the end |
| Monopotassium phosphate (1%) | 400 to 1400 ml/h from 0 to 25 h |
| | 1500 to 5000 ml/h from 25 to 50 h |
| | 300 ml/h from 50 h to the end |
| Sterile water | 630 ml/h from 32 to 100 h |
| | 1260 ml/h from 100 h to the end |

EXAMPLE 25

The procedure is as in Example 21. The fermentation is extended up to 150 h and extractions are carried out in a proportion of 9% every 24 h. The addition of glycerol is omitted completely and the addition of the triglyceride Priolube is increased. The additions of phosphate and sterile water are identical to those in Example 22. The addition of Priolube is according to the following programme:

| | |
|---|---|
| Priolube | 320 ml/h from 10 to 100 h |
| | 590 ml/h from 100 h to the end |

What is claimed is:

1. In a process for the production of clavulanic acid or a salt thereof which comprises (a) culturing a strain of *Streptomyces clavuligerus* in a fermentation medium containing nutrients suitable for said culturing, and (b) isolating the clavulanic acid or salt thereof from the fermentation medium, the improvement comprising providing the fermentation medium at an initial stage with an initial soluble phosphate concentration of between 150 and 600 mg/l and, after the initial stage, maintaining the fermentation medium with a soluble phosphate concentration between 20 and 150 mg/l by adding soluble phosphate to or removing soluble phosphate from the medium.

2. A process as claimed in claim 1, wherein said process comprises adding soluble phosphate to the medium after the initial stage.

3. A process as claimed in claim 2, wherein the culturing is carried out under aeration conditions that provide for a dissolved oxygen concentration above 40% in the fermentation medium at least in the initial stage.

4. A process as claimed in claim 3, wherein said nutrients comprise a source of assimilable carbon that includes one or more triglycerides.

5. A process as claimed in claim 3, wherein the culturing is carried out at a temperature of between 20–40° C.

6. A process as claimed in claim 1, wherein said process comprises removing soluble phosphate from said fermentation medium after the initial stage.

7. A process as claimed in claim 6, wherein said soluble phosphate is removed from the fermentation medium by precipitation with a calcium compound.

8. A process as claimed in claim 1, wherein the *Streptomyces clavuligerus* is ATCC 27064 or a mutant thereof that produces clavulanic acid.

9. A semi continuous or continuous process for the production of clavulanic acid or a salt thereof comprising
   (a) an initial stage comprising culturing a strain of *Streptomyces clavuligerus* in a fermentation medium containing an initial concentration of nutrients and an initial soluble phosphate concentration between 150 and 600 mg/l;
   (b) subsequently introducing an additional concentration of nutrients into the fermentation medium with continued culturing of the strain; and (c) isolating the clavulanic acid or salt thereof from the fermentation medium, said process further comprising controlling a soluble phosphate concentration in the fermentation medium to optimize the production of the clavulanic acid or salt thereof by maintaining the fermentation medium with a soluble phosphate concentration within a range of 20–150 mg/l after the initial stage by adding soluble phosphate to or removing soluble phosphate from the medium.

10. A process as claimed in claim 9, wherein the culturing in at least step (a) is carried out under aeration conditions that provide for a dissolved oxygen concentration above 40% in the fermentation medium.

11. A process as claimed in claim 10, portions of the fermentation medium are continuously or intermittently extracted throughout the process, and wherein said additional concentration of nutrients are introduced into the fermentation medium with water in an amount effective to dilute the fermentation medium sufficiently to maintain a dissolved oxygen concentration in the medium above 40%.

12. A process as claimed in claim 11, wherein the initial soluble phosphate concentration is between 200 to 400 mg/l.

13. A process as claimed in claim 9, wherein the *Streptomyces clavuligerus* strain is ATCC 27064 or a mutant thereof that produces clavulanic acid.

14. A process as claimed in claim 13, wherein the initial concentration of nutrients and the additional concentration of nutrients comprise a source of assimilable carbon that includes one or more triglycerides.

15. A process as claimed in claim 9, comprising adding soluble phosphate to the medium after the initial stage to maintain the soluble phosphate concentration within the range of 20–150 mg/l.

16. In a batch process for the production of clavulanic acid or a salt thereof which consists essentially of (a) culturing a strain of *Streptomyces clavuligerus* in a fermentation medium containing nutrients suitable for said culturing, and (b) thereafter, isolating the clavulanic acid or salt thereof from the fermentation medium, the improvement comprising increasing the production of clavulanic acid or salt thereof by providing the fermentation medium with an initial soluble phosphate concentration between 800 and 1600 mg/l.

17. A process as claimed in claim 16, wherein the culturing is carried out at a temperature of between 20–40° C. and under aeration conditions which provide for a dissolved oxygen concentration above 40% in the fermentation medium.

18. A process as claimed in claim 16, wherein said nutrients comprise a source of assimilable carbon that includes one or more triglycerides.

19. A process as claimed in claim 16, wherein the *Streptomyces clavuligerus* is ATCC 27064 or a mutant thereof that produces clavulanic acid.

* * * * *